United States Patent

Eckstein

[11] Patent Number: 4,812,569
[45] Date of Patent: Mar. 14, 1989

[54] CHROMOGENIC PHTHALIDES

[75] Inventor: Udo Eckstein, Cologne, Fed. Rep. of Germany

[73] Assignee: Bayer Aktiengesellschaft, Leverkusen, Fed. Rep. of Germany

[21] Appl. No.: 20,292

[22] Filed: Feb. 27, 1987

[30] Foreign Application Priority Data

Mar. 20, 1986 [DE] Fed. Rep. of Germany ....... 3609344

[51] Int. Cl.$^4$ .......................................... C07D 405/14
[52] U.S. Cl. ........................................ 546/94; 544/73;
544/74; 544/89; 544/101; 544/105; 544/283;
544/344; 544/353; 546/104; 546/165; 546/166;
546/167; 548/217; 548/220; 548/327; 548/328;
548/439; 548/456
[58] Field of Search ................ 546/94, 104, 165, 166, 546/167

[56] References Cited

U.S. PATENT DOCUMENTS

| | | | |
|---|---|---|---|
| 3,931,227 | 1/1976 | Borror et al. | 548/456 |
| 4,094,877 | 6/1978 | Crounse et al. | 549/309 X |
| 4,349,679 | 9/1982 | Garner et al. | 548/456 X |
| 4,436,920 | 3/1984 | Sato et al. | 548/456 X |

*Primary Examiner*—Richard L. Raymond
*Attorney, Agent, or Firm*—Sprung Horn Kramer & Woods

[57] ABSTRACT

Chromogenic phthalides of the general formula

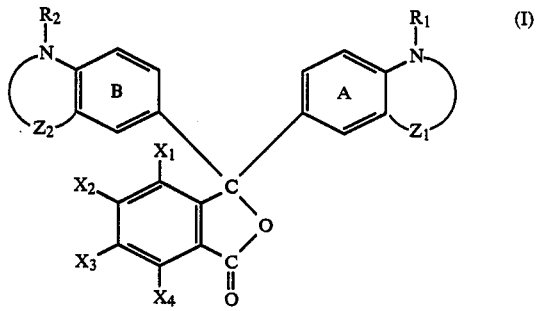

wherein $R_1$ and $R_2$ independently of one another denote hydrogen, alkyl, alkenyl, aralkyl, cycloalkyl or aryl or are linked to the ring A or B respectively in the o-position to the nitrogen and then represent the remaining members of a partially or fully hydrogenated heterocyclic 5-membered or 6-membered ring which can contain a further heteroatom from the series O, S, N—$R_1$ or N—$R_2$, $X_1$, $X_2$, $X_3$ and $X_4$ independently of one another denote hydrogen, halogen, alkyl, alkenyl, aralkyl, cycloalkyl, aryl, hydroxyl, alkoxy, alkenyloxy, aralkoxy, cycloalkoxy, aryloxy, acyloxy, alkylmercapto, arylmercapto, aralkylmercapto, alkylsulphonyl, alkoxycarbonyl or nitro or $X_1+X_2$, $X_2+X_3$ or $X_3+X_4$ denote a fused benzene ring, $Z_1$ and $Z_2$ independently of one another represent the remaining members of a partially or fully hydrogenated heterocyclic 5-membered or 6-membered ring which can contain a further heteroatom from the series O, S, N—$R_1$ or N—$R_2$, and, if $Z_1$ and $Z_2$ represent an optionally substituted C-2 or C-3 alkylene chain, one of the members $Z_1$ and $Z_2$ must carry at least one non-ionic substituent, and the cyclic and acyclic radicals as well as the rings A and B can carry further non-ionic substituents customary in dyestuffs chemistry, are used in pressure-copyable and thermoreactive recording materials.

6 Claims, No Drawings

CHROMOGENIC PHTHALIDES

The invention relates to chromogenic phthalides of the general formula

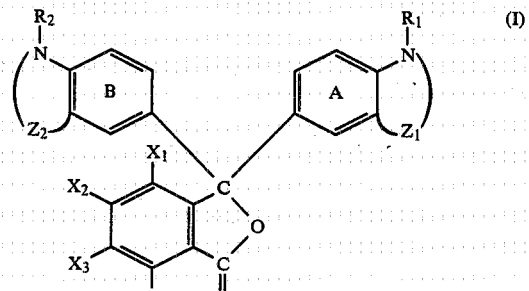

wherein
$R_1$ and $R_2$ independently of one another denote hydrogen, alkyl, alkenyl, aralkyl, cycloalkyl or aryl or are linked to the ring A or B respectively in the o-position to the nitrogen and then represent the remaining members of the partially or fully hydrogenated heterocyclic 5-membered or 6-membered ring which can contain a further heteroatom from the series O, S, N—$R_1$ or N—$R_2$, $X_1$, $X_2$, $X_3$ and $X_4$ independently of one another denote hydrogen, halogen, alkyl, alkenyl, aralkyl, cycloalkyl, aryl, hydroxyl, alkoxy, alkenyloxy, aralkoxy, cycloalkoxy, aryloxy, acyloxy, alkylmercapto, arylmercapto, aralkylmercepto, alkylsulphonyl, alkoxycarbonyl or nitro or $X_1+X_2$, $X_2+X_3$ or $X_3+X_4$ denote a fused benzene ring,
$Z_1$ and $Z_2$ independently of one another represent the remaining members of a partially or fully hydrogenated heterocyclic 5-membered or 6-membered ring which can contain a further heteroatom from the series O, S, N—$R_1$ or N—$R_2$,
and, if $Z_1$ and $Z_2$ represent an optionally substituted C-2 or C-3 alkylene chain, one of the members $Z_1$ and $Z_2$ must carry at least one non-ionic substituent, and the cyclic and acyclic radicals as well as the rings A and B can carry further non-ionic substituents customary in dyestuffs chemistry, to mixtures thereof, to their preparation and to their use in pressure-copyable and thermoreactive recording materials.

Examples of non-ionic substituents customary in dyestuffs chemistry are: halogen, hydroxyl, alkoxy, aryloxy, aralkoxy, heteroaryloxy, aryl, heteryl, alkylmercapto, arylmercapto, aralkylmercapto, alkylsulphonyl, cyano, carbamoyl, alkoxycarbonyl, amino which can be monosubstituted or disubstituted by alkyl, aryl or aralkyl groups or the substituents of which can be cyclized, alkenyloxy, alkylcarbonyloxy and arylcarbonyloxy and, as substituents of the rings, also alkyl, aralkyl, nitro, alkenyl or arylvinyl.

Alkyl preferably represents $C_1$-$C_{30}$-alkyl, in particular $C_1$-$C_{12}$-alkyl and very especially $C_1$-$C_4$-alkyl, and alkenyl preferably represents $C_2$-$C_5$-alkenyl.

Halogen is to be understood in particular as chlorine and bromine.

The alkyl radicals, and the alkyl radicals in alkoxy, alkyl, dialkylamino, alkanoylamino, alkylsulphonyl and alkoxycarbonyl groups, can be branched and be substituted, for example, by fluorine, chlorine, $C_1$- to $C_4$-alkoxy, cyano, or $C_1$-$C_4$-alkoxycarbonyl.

Aralkyl is especially phenyl-$C_1$- to $C_4$-alkyl which can be substituted in the phenyl nucleus by halogen, $C_1$-$C_4$-alkyl and/or $C_1$- to $C_4$-alkoxy.

Cycloalkyl is in particular cyclopentyl or cyclohexyl optionally substituted by methyl.

Aryl is in particular phenyl or naphthyl, which are optionally monosubstituted to trisubstituted by $C_1$- to $C_4$-alkyl, chlorine, bromine, cyano, $C_1$- to $C_4$-alkoxycarbonyl or $C_1$- to $C_4$-alkoxy.

Alkoxy is in particular $C_1$-$C_{12}$-alkoxy which is optionally substituted by chlorine or $C_1$-$C_4$-alkoxy.

Acyl is in particular $C_1$- to $C_4$-alkylcarbonyl and $C_1$- to $C_4$-alkoxycarbonyl, or aminocarbonyl or aminosulphonyl optionally monosubstituted or disubstituted by $C_1$-$C_4$-alkyl, phenyl or benzyl.

Alkoxycarbonyl is in particular $C_1$- to $C_4$-alkoxycarbonyl which is optionally substituted by hydroxyl, halogen or cyano.

Together with the fused heterocyclic rings, the rings A and B preferably represent dihydroquinoline, tetrahydroquinoline, tetrahydroquinoxaline, tetrahydroquinazoline, tetrahydrophenoxazine, tetrahydrophenazine, tetrahydroacridine, hexahydro- and tetrahydro-carbazole, tetrahydrobenzothiazine, tetrahydrobenzoxazine, tetrahydroisobenzoxazine, dihydrobenzimidazole, dihydrobenzoxazole, dihydrobenzothiazole, indoline, julolidine and lilolidine.

The rings can be substituted by non-ionic substituents, in particular by $C_1$-$C_{12}$-alkyl, $C_1$-$C_4$-alkoxy, chlorine, cyano or nitro.

Of the compounds of the formula (I), the compounds of the formula

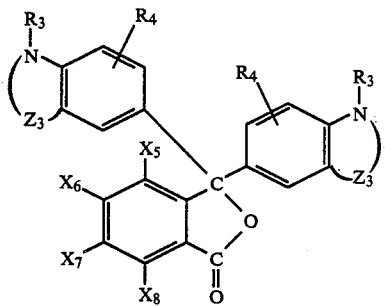

are of particular importance, wherein the two radicals

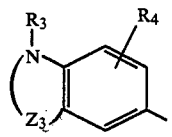

are identical or different and represent

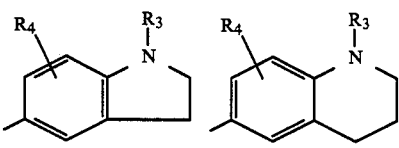

-continued

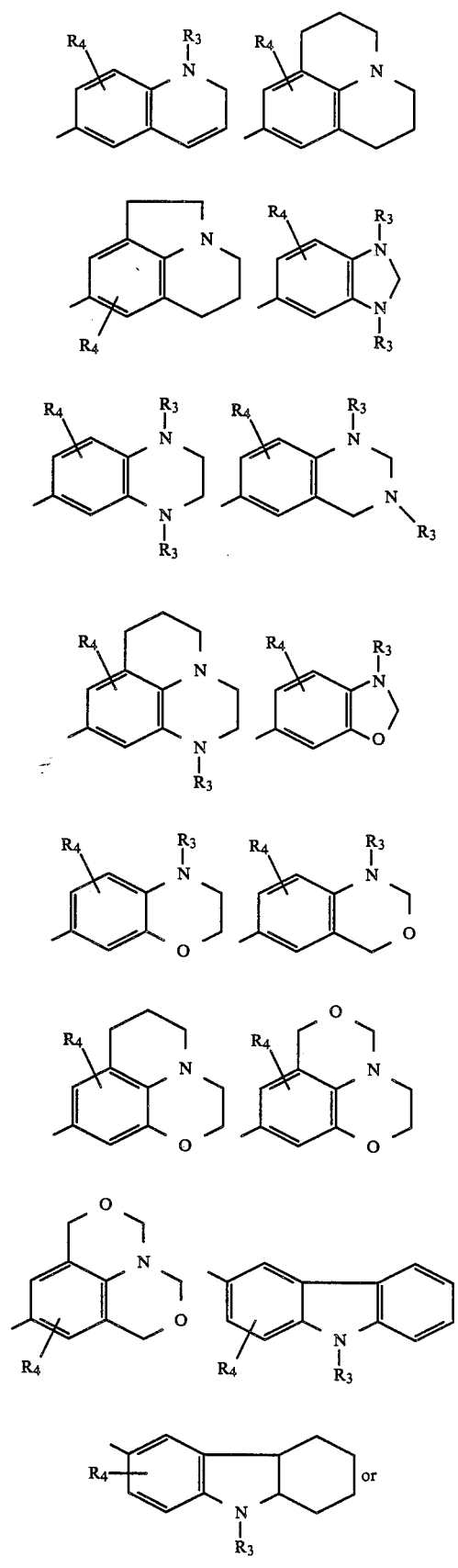

-continued

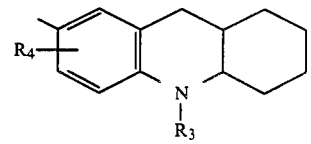

wherein the (partially) saturated rings can carry up to 4 radicals from the group comprising chlorine, $C_1$–$C_4$-alkyl, $C_1$–$C_4$-alkoxy or phenyl and, in the case of indoline, tetrahydroquinoline and julolidine, the saturated rings must carry at least one of these radicals, $R_3$ denotes hydrogen, $C_1$–$C_{12}$-alkyl which is optionally substituted by chlorine, hydroxyl, $C_1$–$C_4$-alkoxy or acetyloxy, cyclohexyl, $C_1$–$C_4$-alkylcarbonyl or benzyl or phenyl which are optionally substituted by chlorine of $C_1$–$C_4$-alkyl, $R_4$ denotes hydrogen, chlorine, $C_1$–$C_4$-alkyl, $C_1$–$C_4$-alkoxy, amino which can be optionally monosubstituted or disubstituted by chlorine, cyano, $C_1$–$C_4$-alkoxycarbonyl, hydroxyl or $C_1$–$C_4$-alkoxysubstituted $C_1$–$C_4$-alkyl, cyclohexyl, phenyl or benzyl groups, and $X_5$, $X_6$, $X_7$ and $X_8$ independently of one another denote hydrogen, chlorine, $C_1$–$C_4$-alkyl, $C_1$–$C_4$-alkoxy, hydroxyl or phenyl, benzyl or benzyloxy which are optionally substituted by chlorine, $C_1$–$C_4$-alkyl or $C_1$–$C_4$-alkoxy.

Examples of radicals (1) are:

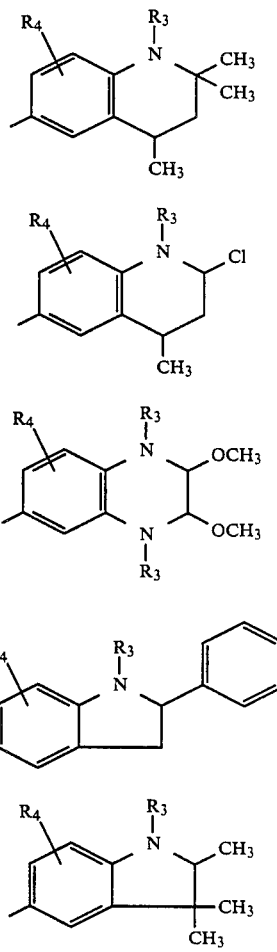

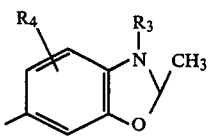

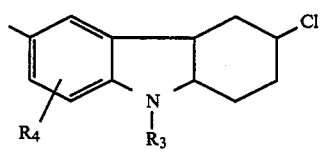

Particularly preferred compounds correspond to the formula

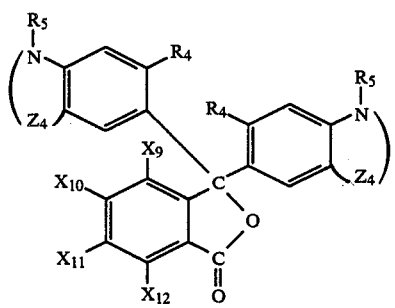

(III)

wherein the two radicals

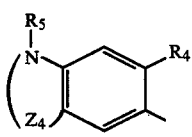

(2)

are identical or different and represent

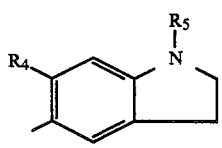

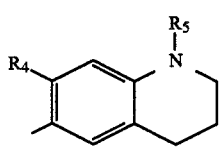

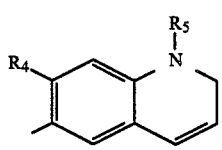

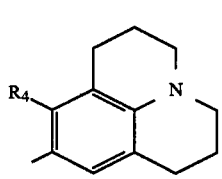

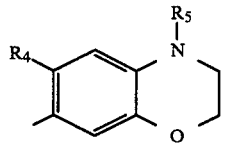

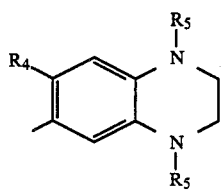

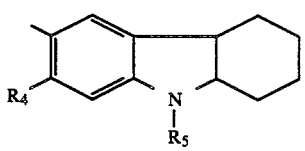

wherein $R_4$ has the meaning given above and the (partially) saturated rings carry up to 4 radicals from the group comprising chlorine, $C_1$–$C_4$-alkyl, $C_1$–$C_4$-alkoxy or phenyl and, in the case of indoline, tetrahydroquinoline and julolidine, the saturated rings must carry at least one of these radicals, $R_5$ denotes hydrogen, or $C_1$–$C_{12}$-alkyl or benzyl which are optionally substituted by chlorine, hydroxyl, methoxy, ethoxy or acetyloxy, and $X_9$, $X_{10}$, $X_{11}$ and $X_{12}$ independently of one another denote hydrogen, chlorine, $C_1$–$C_4$-alkyl, $C_1$–$C_4$-alkoxy, phenyl or benzyl.

Of the compounds (III) those are to be singled out in which the radicals (2) are identical. Amongst these compounds, very particularly preferred compounds correspond to the formula

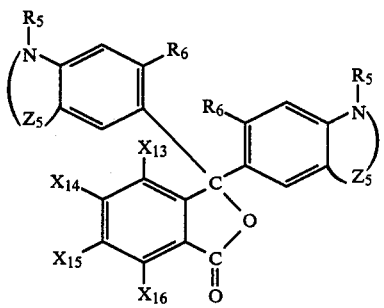

(IV)

wherein the radicals

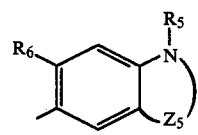

represent

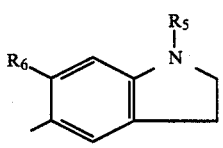

-continued

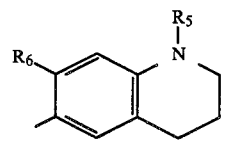

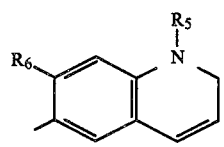

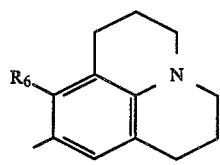

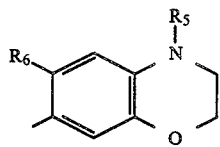

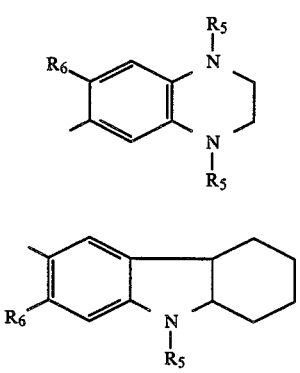

wherein
$R_5$ has the meaning given above,
$R_6$ is hydrogen, chlorine, methyl, ethyl, methoxy, ethoxy or amino which can be optionally monosubstituted or disubstituted by $C_1$–$C_4$-alkyl groups substituted by chlorine, cyano, hydroxyl, methoxy or ethoxy, $X_{13}$, $X_{14}$, $X_{15}$ and $X_{16}$ independently of one another denote hydrogen, chlorine, methyl, ethyl, methoxy, ethoxy or phenyl,
the (partially) hydrogenated rings can carry up to 4 radicals from the group comprising chlorine, methyl, ethyl, methoxy, ethoxy or phenyl and, in the case of indoline, tetrahydroquinoline and julolidine, the saturated rings must carry at least one of these radicals.

Mixtures of the unsymmetrical and the two symmetrical compounds of the formula (III) are also of particular industrial interest.

The invention also relates to a process for the preparation of the phthalides of the formula (I) which is characterized in that, in a one-pot reaction, anhydrides of the formula

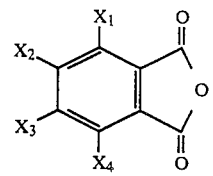

are condensed either simultaneously or successively with amines of the formula(e)

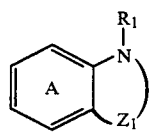

and/or

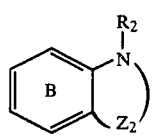

in a reaction medium suitable for the condensation and in the presence of catalysts to give ketocarboxylic acids of the formula(e)

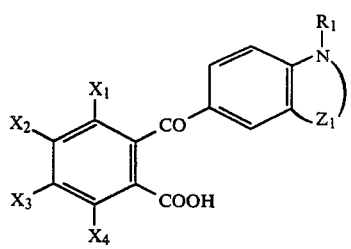

and/or

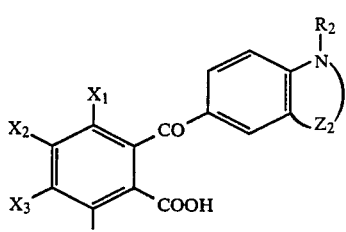

and these are reacted, without intermediate isolation and with the addition of dehydrating condensing agents, with further amines of the formula(e) (VIa) and/or (VIb) to give compounds of the formula (I), wherein the symbols have the meaning given above.

In this way, symmetrical and unsymmetrical compounds of the formula (I) and mixtures of symmetrical and unsymmetrical compounds of the formula (I) can be prepared.

The compounds according to the invention, of the formula (I), and their mixtures are usually also obtained when the ketocarboxylic acids of the formula(e) (VIIa) and/or (VIIb) are isolated and condensed with the corresponding amines (VIa) and/or (VIb) in acetic anhydride.

After complete reaction, the reaction mixture, if necessary also after removal of the inert solvents, is discharged onto, for example, water or a lower alkanol. By raising the pH value by means of, for example, alkali or alkaline earth metal hydroxides, carbonates or bicarbonates, ammonia or amines until the colour of the mixture vanishes, the phthalides of the formula (I) or their mixtures are obtained, which are either isolated in the customary manner or separated off in the organic phase. After removal of the particular solvent and further stirring in alkanols, for example methanol, ethanol, propanol or butanol, in nitriles, for example acetonitrile, in ketones, for example acetone or 2-butanone, in esters, for example ethyl acetate or butyl acetate, or in ethers, for example diisopropyl ether or di-sec.-butyl ether, the phthalides of the formula (I) or their mixtures are obtained in high yields and excellent quality.

Suitable solvents are aromatic hydrocarbons such as toluene or xylene, chlorobenzene, o-dichlorobenzene, chlorotoluene or nitrobenzene, halogenohydrocarbons such as dichloroethane, trichloroethylene, methylene chloride or carbon tetrachloride, carbon disulphide or glacial acetic acid.

Examples of suitable catalysts are $AlCl_3$, $FeCl_3$, $SnCl_4$, $BF_3$, $TiCl_3$, $ZnCl_2$, $H_2SO_4$ or $H_3PO_4$.

Suitable dehydrating condensing agents are alkanoic acid anhydrides such as acetic anhydride, propionic anhydride or trichloroacetic anhydride, sulphuric acid, p-toluenesulphonic acid, polyphosphoric acid or phosphorus pentoxide. Suitable reaction temperatures are between 20° and 180° C., and 30° to 120° C. are preferred.

The phthalides of the formula (I) or their mixtures are normally colourless or at most slightly coloured.

When these colour formers are brought into contact with a preferably acidic developer, that is to say an electron acceptor, intense blue, green-blue, green or violet colour shades, which show excellent fastness to sublimation and light, are obtained.

They are also valuable as a mixture with one or more other known colour formers, for example 3,3-bis-(aminophenyl)-phthalides, 3,3-bis-(indolyl)-phthalides, 3-aminofluorans, 2,6-diaminofluorans, leucoauramines, spiropyrans, spirodipyrans, chromenoindoles, phenoxazines, phenothiazines, carbazolylmethanes or other triarylmethane leuco dyestuffs, in order to give green, violet, blue, navy blue, grey or black colorations.

Both on phenolic substrates and salicylate substrates and especially on activated clays, the phthalides of the formula (I) or their mixtures give good colour intensity and light fastness. They are suitable above all as colour formers for use in a heat-sensitive or pressure-sensitive recording material which can be either a copying material or a registering material. Their development speed varies as a function of the substituents. In general, however, they are distinguished by a high developing speed, coupled at the same time with a reduced sensitivity of the recording materials to inadvertent premature development.

Typical examples of developers in pressure-sensitive materials are inorganic substances, such as clays, metal salts or metal oxides or organic polymers such as phenolic resins.

The compounds of the formula (I) or mixtures thereof are preferably also used as colour formers in a thermoreactive recording material.

Thermoreactive recording systems comprise, for example, heat-sensitive recording and copying materials and papers. These systems are used, for example, for the recording of information, for example in electronic computers, teleprinters, telex machines or in recording instruments and measuring instruments such as electrocardiographs. The image generation (marking) can also take place manually, using a heated pen. A further device for generating markings by means of heat are laser beams.

Suitable developers are the same electron acceptors as used in pressure-sensitive papers, preferably phenolic compounds, which are described, for example, in German Patent Specification No. 1,251,348, as well as boric acid and organic, preferably aliphatic dicarboxylic acids.

Fusible, film-forming binders, which are soluble or swellable in water, are preferably used for the preparation of the thermoreactive recording material. Under the action of heat, the binder softens or melts, so that the colour former comes into contact with the developer and can form a colour. Examples of suitable binders are hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

The process and preparations described are known, for example, from U.S. Pat. Nos. 2,800,457, 2,800,458, 2,946,753, 3,096,189 and 3,193,404 and from German Offenlegungsschriften Nos. 2,555,080 and 2,700,937.

The phthalides of the formula (I) or the dyestuffs formed from them by ring-opening are suitable for dyeing polyacrylonitrile, tanned cotton and other acid-modified fibres, fabrics and powders.

EXAMPLE 1

13.7 g (0.1 mol) of powdered aluminium chloride (98% pure) are added in portions to 14.8 g (0.1 mol) of phthalic anhydride and 24.4 g (0.12 mol) of 1-ethyl-2,2,4-trimethyl-1,2,3,4-tetrahydroquinoline in 100 ml of anhydrous chlorobenzene, in such a way that the temperature does not exceed 30° C. The mixture is stirred for 1 hour at 30° C. and 1 hour at 60° C. The reaction mixture is then subjected to a steam distillation. Cooling and filtration with suction gives 20.5 g (58.4% of theory) of crude product, of melting point 213°–218° C., of the ketocarboxylic acid of the formula

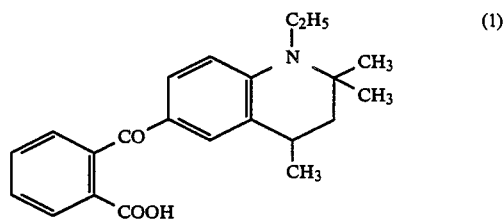

which can be reprecipitated from 70% strength acetic acid; yellowish crystals of melting point 221°–23° C.

10.5 g (0.03 mol) of the ketocarboxylic acid of the formula (1) and 6.1 g (0.03 mol) of 1-ethyl-2,2,4-trimethyl-1,2,3,4-tetrahydroquinoline are stirred in 50 ml of acetic anhydride for 2 hours at 100° C. After cooling, 50 ml of ethanol are added, the solution is discharged onto 250 ml of 10% strength sodium hydroxide solution and the mixture is stirred for 1 hour, intensively washed with ethanol and dried: 14.1 g (87.6%) of theory) of colourless powder of melting point 118° to 123° C. of the formula

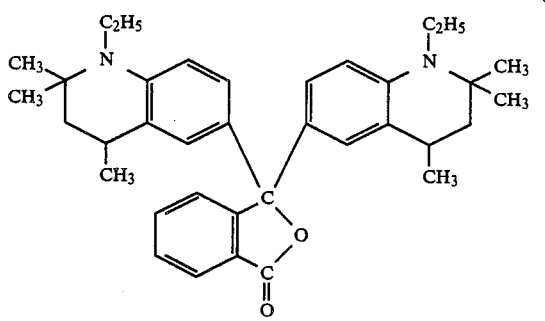

(2)

from hexane, colourless crystals of melting point: 131°–34° C.

$C_{36}H_{44}N_2O_2$ (536.7) calculated: 80.55% C, 8.3% H, 5.2% N. found: 80.5% C, 8.5% H 5.0% N.

A solution in glacial acetic acid turns green, with $\lambda_{max}=652$ nm and $\lambda_2=420$ nm.

On acid clay or bisphenol A, a deep green colour with good fastness properties is developed.

EXAMPLE 2

22.3 g (0.11 mol) of 1-ethyl-2,2,4-trimethyl-1,2,3,4-tetrahydroquinoline and 7.4 g (0.05 mol) of phthalic anhydride are dissolved in 100 ml of anhydrous chlorobenzene, and 7 g (0.05 mol) of aluminium chloride (95% pure) are added in portions at room temperature. The room temperature is maintained by external cooling. The mixture is then stirred for a further 4 hours at 60° C. After the addition of 30 g of acetic anhydride, the mixture is stirred for another 4 hours at this temperature. The reaction mixture is discharged onto 500 ml of ice-water and the chlorobenzene phase is separated off. The latter is decolourized with 100 ml of 10% strength sodium hydroxide solution, extracted by shaking with 100 ml of water and separated off. After removal of the solvent in vacuo, 80 ml of methanol are added to the oily residue, the mixture is stirred for 1 hour and filtered with suction, and the product is washed with methanol and dried. 24.2 g (90.3% of theory) of colourless crystals of melting point 134°–136° C., of the formula (2).

EXAMPLE 3

Replacing 1-ethyl-2,2,4-trimethyl-1,2,3,4-tetrahydroquinoline in the above example by the corresponding quantity of 1,2,2,4-tetramethyl-1,2,3,4-tetrahydroquinoline and following the procedure as indicated, 19.8 g (78% of theory) of colourless crystals of the compound of the formula

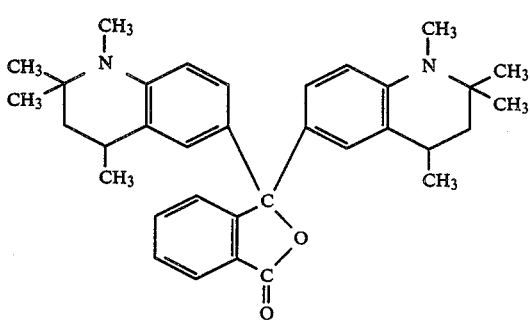

(3)

are obtained, which has a melting point of 141°–45° C. and develops a deep green colour on acid clay, bisphenol A and salicylate. Absorption spectrum in glacial acetic acid: $\lambda_{max}=646$ nm and $\lambda_2=420$ nm.

EXAMPLE 4

17.5 g (0.01 mol) of 1,2,3,3-tetramethyl-indoline and 7.4 g (0.05 mol) of phthalic anhydride are dissolved in 100 ml of anhydrous chlorobenzene, and 7 g (0.05 mol) of aluminium chloride (95% pure) are added. The temperature is first held at 30° C. for 1 hour, and the mixture is then stirred for 3 hours at 60° C. After the addition of 20 g of acetic anhydride, stirring is continued for a further 2 hours at 60° C. The reaction mixture is diluted with 200 ml of chlorobenzene and discharged onto 500 ml of ice water. 200 ml of 20% strength sodium hydroxide are then added dropwise, and the mixture is stirred at room temperature until the organic phase has been decolourized. The organic phase is separated off, the solvent is removed in vacuo and 100 ml of methanol are added to the residue. Filtration with suction, washing with a little methanol and drying gives almost colourless crystals of melting point 163°–166° C., of the formula

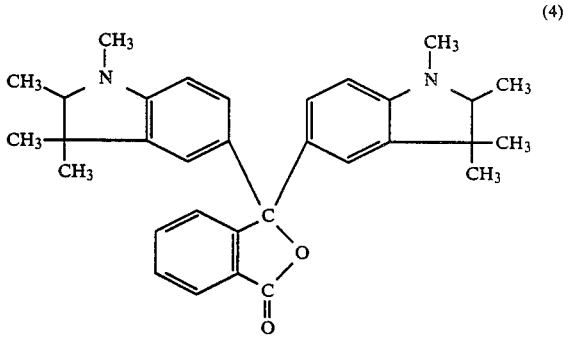

(4)

which can be recrystallized from methanol.

On bisphenol A, salicylate and acid clay, a dark green coloration is obtained immediately.

The following phthalides of the formula

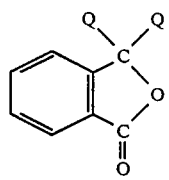

are prepared analogously to Examples 2, 3 and 4.

| Formula No. | Q | Colour shade on acid clay or bisphenol A | $\lambda_{max}$ in glacial acetic acid |
|---|---|---|---|
| 5 | 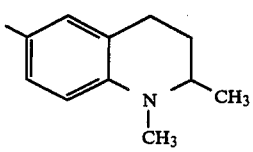 | green | 644 nm |
| 6 | 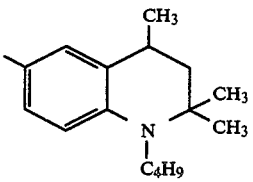 | green | 652 nm |
| 7 | 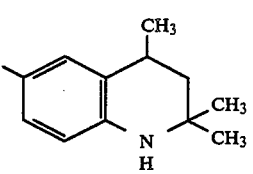 | blue green | 621 nm |
| 8 | 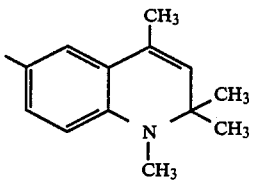 | dark green | 680 nm |
| 9 | 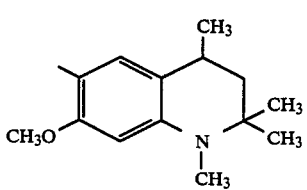 | blue green | 660 nm |
| 10 | 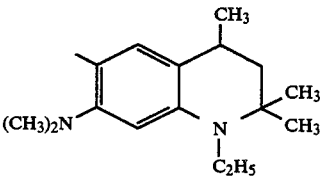 | blue | 635 nm |
| 11 | 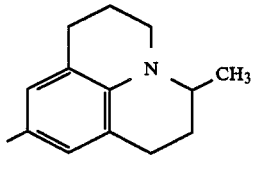 | dark green | 668 nm |
| 12 | 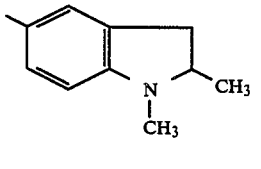 | green | 647 nm |
| 13 | 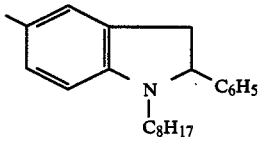 | green | 650 nm |

| Formula No. | Q | Colour shade on acid clay or bisphenol A | $\lambda_{max}$ in glacial acetic acid |
| --- | --- | --- | --- |
| 14 | ![structure] | black green | 720 nm |
| 15 | ![structure] | blue green | 685 nm |
| 16 | ![structure] | green | 638 nm |

EXAMPLE 5

7 g (0.05 mol) of aluminium chloride (95% pure) are added in portions to the solution of 20.3 g (0.1 mol) of 1-ethyl-2,2,4-trimethyl-1,2,3,4-tetrahydroquinoline and 14.3 g (0.05 mol) of tetrachlorophthalic anhydride in 100 ml of anhydrous 1,2-dichlorobenzene. During the addition, the temperature is kept at 25° C., and the mixture is stirred for 1 hour at this temperature. After 2 hours, 30 g of acetic anhydride are added dropwise at 60° C. and the mixture is stirred for a further 2 hours at 60° C. The reaction mixture is diluted with 300 ml of 1,2-dichlorobenzene, discharged onto 700 ml of ice-water and separated. The organic phase is extracted by shaking with twice 100 ml 10% strength sodium hydroxide solution and 100 ml of water and separated off. After removal of the solvent in vacuo, the residue is stirred up with 100 ml of methanol, filtered off with suction, washed with methanol and dried. This gives 33 g (98% of theory) of yellow crystals of melting point 220°–25° C. and of the formula

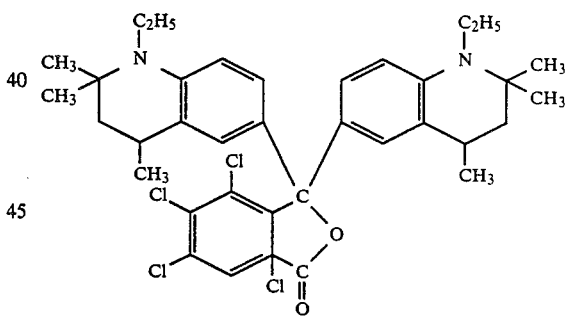
(17)

which are recrystallized from methylcyclohexane. Melting point: 227°–29° C.

On acid clay and bisphenol A, deep green colour shades are obtained.

The phthalides of the formula

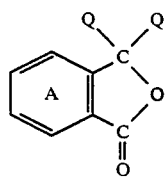

are also obtained as described in Example 5.

| Formula No. | Substituents of ring A | Q | Colour shade on acid clay or bisphenol A | $\lambda_{max}$ in glacial acetic acid |
|---|---|---|---|---|
| 18 | Isomer mixture of 5-OCH₃ and 6-OCH₃ | (1,2,2,4-tetramethyl-tetrahydroquinoline, N-CH₃) | blue green | 645 nm |
| 19 | 5-OCH₃ 6-OCH₃ | (N-C₂H₄OCO—CH₃, 2,2,4-trimethyl-tetrahydroquinoline) | blue green | 648 nm |
| 20 | Isomer mixture of 5-Cl and 6-Cl | (N-C₂H₄Cl, 2-methyl indoline) | green | 658 nm |
| 21 | 5-OCH₃ 6-OCH₃ | (CH₃—CO—NH-substituted, N-C₂H₅, 2,2,4-trimethyl-tetrahydroquinoline) | black green | 720 nm |
| 22 | Isomer mixture of 5-C₆H₅ and 6-C₆H₅ | (N-C₁₂H₂₅, 2-methyl indoline) | dark green | 675 nm |
| 23 | Isomer mixture of 5-OCH₃ and 6-OCH₃ | (CH₃O-substituted, N-CH₃, 2,2,4-trimethyl-dihydroquinoline) | dark violet | 660 nm |
| 24 | 5-CH₃ 6-CH₃ | (N-C₃H₇, 2-chloro-4-methyl-tetrahydroquinoline) | dark green | 665 nm |

EXAMPLE 6

8.7 g (0.05 mol) of 1,2,3,3-tetramethyl-indoline, 9.4 g (0.05 mol) of 1,2,2,4-tetramethyl-1,2,3,4-tetrahydroquinoline and 7.4 g (0.05 mol) of phthalic anhydride are dissolved in 100 ml anhydrous chlorobenzene, and 14 g (0.1 mol) of aluminium chloride (95% pure) are added in portions at room temperature. The mixture is stirred for 4 hours at 60° C., 20 g of acetic anhydride are added, and stirring is continued for a further 2 hours at 60° C. The reaction mixture is discharged onto 500 ml of ice-water, and the organic phase is separated off. 100 ml of 10% strength sodium hydroxide solution are added to the organic phase, the mixture is stirred for 20 minutes and the organic phase is separated off again. After removal of the solvent in vacuo, 50 ml of methanol are added to the above residue, the mixture is stirred for 1 hour and the product is filtered off with suction, washed with methanol and dried. This gives 21.3 g of almost colourless crystals of a mixture of the formulae (3), (4) and (25)

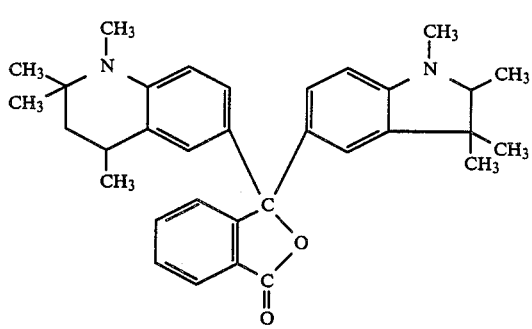

$\lambda_{max}$ = 646 nm
$\lambda_2$ = 422 nm which develops a deep dark green colour on acid clay, bisphenol A and salicylate.

I claim:

1. A chromogenic phthalide of the formula

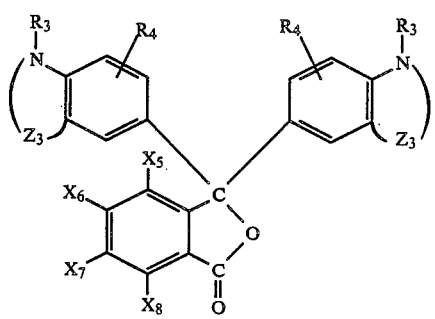

wherein the two radicals

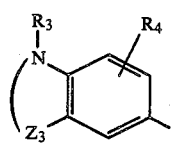

are identical or different and represent

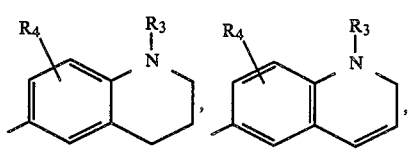

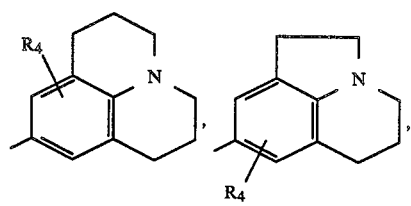

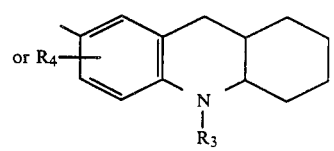

wherein the (partially) saturated rings can carry up to 4 radicals selected from the group consisting of chlorine, $C_1$-$C_4$-alkyl, $C_1$-$C_4$-alkoxy and phenyl and, in the case of tetrahydroquinoline and julolidine, the saturated rings must carry at least one of these radicals, $R_3$ denotes hydrogen, $C_1$-$C_{12}$-alkyl which is unsubstituted or substituted by chlorine, hydroxyl, $C_1$-$C_4$-alkoxy or acetyloxy, cyclohexyl, $C_1$-$C_4$-alkyl-carbonyl or benzyl or phenyl which are unsubstituted or substituted by chlorine or $C_1$-$C_4$-alkyl, $R_4$ denotes hydrogen, chlorine, $C_1$-$C_4$-alkyl, $C_1$-$C_4$-alkoxy, amino which is unsubstituted or mono-substituted or disubstituted by chlorine, cyano, $C_1$-$C_4$-alkoxycarbonyl, hydroxyl or $C_1$-$C_4$-alkoxy substituted $C_1$-$C_4$-alkyl, cyclohexyl, phenyl or benzyl groups, and $X_5$, $X_6$, $X_7$ and $X_8$ independently of one another denote hydrogen, chlorine, $C_1$-$C_4$-alkyl, $C_1$-$C_4$-alkoxy, hydroxyl or phenyl, benzyl or benzyloxy which are unsubstituted or substitututed by chlorine, $C_1$-$C_4$-alkyl or $C_1$-$C_4$-alkoxy.

2. A chromogenic phthalide according to claim 1 of the formula

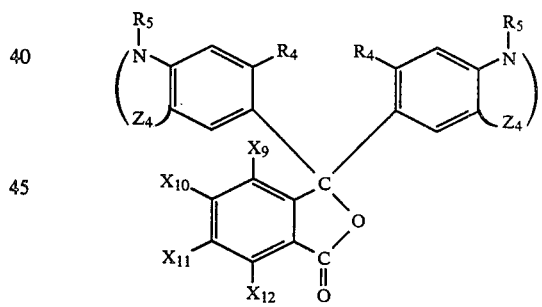

wherein the two radicals

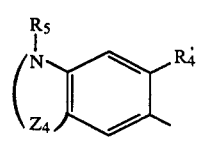

are identical or different and represent

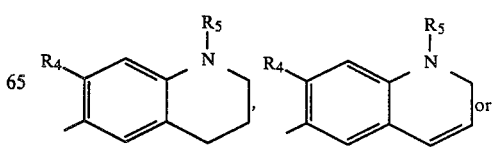

-continued

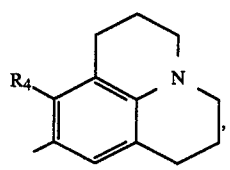

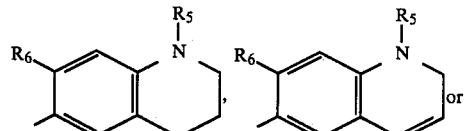

wherein
R₄ has the meaning given in claim 1 and the (partially) saturated rings carry up to 4 radicals selected from the group consisting of chlorine, $C_1$–$C_4$-alkyl, $C_1$–$C_4$-alkoxy and phenyl and, in the case of tetrahydroquinoline and julolidine, the saturated rings must carry at least one of these radicals, R₅ denotes hydrogen, or $C_1$–$C_{12}$-alkyl or benzyl which are unsubstituted or substituted by chlorine, hydroxyl, methoxy, ethoxy or acetyloxy, and X₉, X₁₀, X₁₁ and X₁₂ independently of one another denote hydrogen, chlorine, $C_1$–$C_4$-alkyl, $C_1$–$C_4$-alkoxy, phenyl or benzyl.

3. A chromogenic phthalide according to claim 1, of the formula

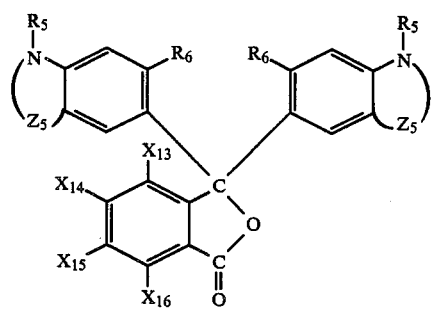

wherein the radicals

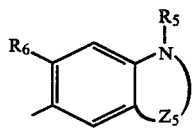

represent

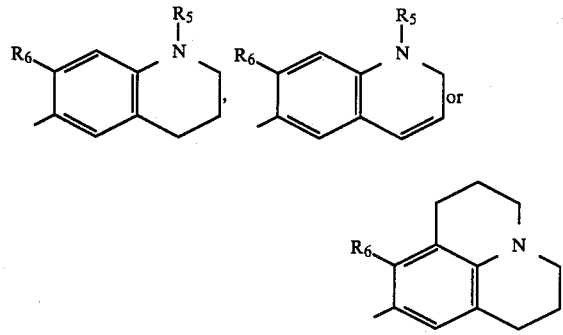

wherein
R₅ denotes hydrogen or $C_1$–$C_{12}$-alkyl or benzyl which are unsubstituted or substituted by chlorine, hydroxyl, methoxy, ethoxy or acetyloxy,
R₆ is hydrogen, chlorine, methyl, ethyl, methoxy, ethoxy or amino which is unsubstituted or monosubstituted or disubstituted by $C_1$–$C_4$-alkyl groups substituted by chlorine, cyano, hydroxyl, methoxy or ethoxy, X₁₃, X₁₄–X₁₅ and X₁₆ independently of one another denote hydrogen, chlorine, methyl, ethyl, methoxy, ethoxy or phenyl,
the hydrogenated rings can carry up to 4 radicals selected from the group consisting of chlorine, methyl, ethyl, methoxy, ethoxy and phenyl and, in the case of tetrahydroquinoline and julolidine, the saturated rings must carry at least one of these radicals.

4. A chromogenic phthalide of the formula of claim 3, wherein

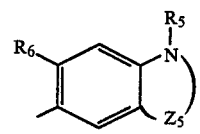

represents

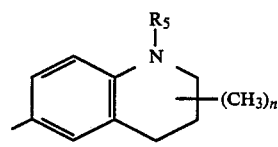

with n=1, 2 or 3.

5. A chromogenic phthlide according to claim 4, wherein n is 3.

6. Mixtures of the phthalides according to claim 2 consisting essentially of symetrical and unsymetrical compounds of the formula of claim 2.

* * * * *

UNITED STATES PATENT AND TRADEMARK OFFICE
CERTIFICATE OF CORRECTION

PATENT NO. : 4,812,569
DATED : March 14, 1989
INVENTOR(S) : Udo Eckstein It is certified that error appears in the above-identified patent and that said Letters Patent is hereby corrected as shown below:

Col. 1, line 32      Delete "aralkylmercepto" and substitute --aralkylmercapto--

Col. 16, line 48      Bottom of formula delete " [structure with Cl] " and substitute -- [structure with Cl] --

Col. 22, line 27      Before "hydrogenated" insert --(partially)--

Signed and Sealed this

Sixth Day of March, 1990

*Attest:*

JEFFREY M. SAMUELS

*Attesting Officer*      *Acting Commissioner of Patents and Trademarks*